United States Patent [19]

Beck

[11] 3,966,812
[45] June 29, 1976

[54] TRICHLOROETHYLIDENE-BIS-(ISOCYANIDE-DICHLORIDE) AND PROCESS FOR MAKING SAME

[75] Inventor: Gunther Beck, Leverkusen, Germany

[73] Assignee: Bayer Aktiengesellschaft, Leverkusen, Germany

[22] Filed: Oct. 28, 1975

[21] Appl. No.: 626,409

[30] Foreign Application Priority Data
Oct. 30, 1974 Germany............................ 2451634

[52] U.S. Cl.............................. 260/566 D; 424/325
[51] Int. Cl.$^2$...................................... C07C 119/00
[58] Field of Search..................................... 260/566

[56] References Cited
UNITED STATES PATENTS

| | | | |
|---|---|---|---|
| 3,267,144 | 8/1966 | Ottmann et al................. | 260/566 D |
| 3,639,479 | 2/1972 | Arlt................................. | 260/566 D |
| 3,795,706 | 3/1974 | Oxenrider et al.............. | 260/566 D |

*Primary Examiner*—Gerald A. Schwartz
*Attorney, Agent, or Firm*—Burgess, Dinklage & Sprung

[57] ABSTRACT

Trichloroethylidene-bis-(isocyanide-dichloride) is prepared by treating trichloroethylidene-bis-formamide with acid chlorides in the presence of an inert diluent at temperatures of about 0° to 150°C. The reaction mixture is then reacted, simultaneously or subsequently, with an excess of chlorine to form the desired product.

1 Claim, No Drawings

TRICHLOROETHYLIDENE-BIS-(ISOCYANIDE-DICHLORIDE) AND PROCESS FOR MAKING SAME

This invention relates to trichloro-ethylidene-bis-(isocyanide-dichloride) and to a process for its preparation.

SUMMARY

It has been found that trichloroethylidene-bis-(isocyanide-dichloride) is obtained when trichloroethylidene-bis-formamide is reacted with acid chlorides in the presence of a diluent and the reaction mixture is simultaneously or subsequently reacted with an excess of chlorine.

DESCRIPTION

In general, it has proved suitable to carry out the process according to the invention at temperatures of about 0°C to 150°C, preferably at about 80°C to 150°C.

Examples of suitable inert diluents are compounds which are chlorine-resistant solvents, for example chlorinated nonpolar aliphatic and aromatic hydrocarbons, especially chloroform carbon tetrachloride, 1,1,2,2-tetrachloroethane, tetrachloroethylene, 1,1,2,3,3-pentachloropropane and 1,2,4-trichlorobenzene. According to a particular embodiment of the process according to the invention, further possible diluents are the compounds used as acid chlorides, such as phosphorus oxychloride, thionyl chloride and sulphuryl chloride, if they are employed in appropriate excess. Particularly preferred diluents are chlorinated non-polar aliphatic hydrocarbons such as, for example, carbon tetrachloride and tetrachloroethylene. In general, 0.5 to 20, preferably 2.5 to 10, parts by volume of the diluent are employed per 1 part by weight of trichloroethylidene-bis-formamide.

Examples which may be mentioned of acid chlorides used for the process according to the invention are the acid chlorides of inorganic acids, preferably thionyl chloride, sulphuryl chloride, phosphorus pentachloride, phosphorus trichloride and phosphorus oxychloride or organic acid chlorides, preferably oxalyl chloride. Phosphorus pentachloride or phosphorus trichloride, in the presence of an excess of chlorine, are particularly preferred. The acid chloride is generally employed in the stoichiometrically required amount or in a slight excess, that is to say about 2 to 2.5 mols of the acid chloride per 1 mol of trichloroethylidene-bis-formamide. Of course, the acid chloride can also be employed in a larger excess, which is the case, for example, if the acid chloride at the same time fulfils the function of the diluent.

The starting compound, trichloroethylidene-bis-formamide, is known (Annales de Chimie et de Physique, 6th series, volume 27, page 326; compare Beilsteins Handbuch der Organischen Chemie (Beilstein's Handbook of Organic Chemistry), 4th edition, volume 2, page 27) and can be prepared, for example, by reaction of 1 mol of chloral with 2 mols of formamide.

The process according to the invention can be represented by the following equation for the example of the reaction of trichloroethylidene-bis-formamide with phosphorus pentachloride:

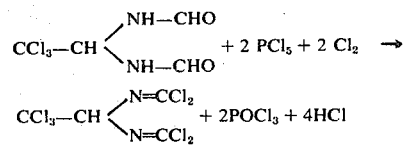

According to a particularly preferred embodiment of the process according to the invention, trichloroethylidene-bis-formamide is added gradually to a mixture of diluent and acid chloride, saturated with chlorine gas, which is boiling under reflux, whilst constantly continuing to pass in chlorine gas, the gradual addition being such that the reaction takes place in a controlled manner and that an excess of chlorine constantly remains in the reaction mixture. After completion of the addition of trichloroethylidene-bis-formamide, the mixture is heated to about 150°C in the course of about 1 to 3 hours under reflux, while continuing to pass in chlorine gas, the diluent is distilled off and the reaction mixture is worked up.

According to a variant of this embodiment it is, however, also possible initially to introduce trichloroethylidene-bis-formamide into the particularly preferred diluent which is boiling under reflux and through which excess chlorine gas is flowing, and to meter in the acid chloride gradually, or initially to introduce the diluent which is boiling under reflux and is saturated by chlorine gas passing through it, and to meter in both the acid chloride and the trichloroethylidene-bis-formamide.

To carry out the process according to the invention, it has proved particularly advantageous if the reaction with the acid chloride takes place simultaneously with the addition of the chlorine gas and the reaction temperature maintained is the particular boiling point of the diluent.

The working up of the reaction mixture can be effected, for example, by means of fractional vacuum distillation, in which case phosphorus pentachloride which may still be present in excess is converted, prior to working up, into phosphorus oxychloride and thionyl chloride, which can easily be removed by distillation, through reaction with sulphur dioxide in a manner which is in itself known. In this way, trichloroethylidene-bis-(isocyanide-dichloride) can easily be separated off, since the possible decomposition products of the reaction boil at a substantially lower temperature and any possible condensation products boil at a substantially higher temperature.

The trichloroethylidene-bis-(isocyanide-dichloride) according to the invention is new and can be used as a fungicide and as an insecticide (see Example 9 herein).

In addition, because of its bifunctionality, the compound of the invention is a valuable intermediate product and is suitable for the synthesis of heat-resistant and flameproof plastics, for example those based on condensation products with diols or polyols, or diamines or polyamines.

The following Examples illustrate the invention:

EXAMPLE 1

439 g (2 mols) of trichloroethylidene-bis-formamide were added in small portions, over the course of about 2–3 hours, to a suspension, boiling under reflux and saturated with chlorine gas, of 1,000 g (4.8 mols) of phosphorus pentachloride in 2,000 ml of carbon tetrachloride, whilst excluding moisture and constantly continuing to pass in excess chlorine; in the course of this, the boiling point of the mixture rose to 84°C. Whilst continuing to pass in excess chlorine, carbon tetrachloride and phosphorus oxychloride formed in the reaction were distilled off over the course of about 1.5 to 2 hours, during which the temperature was raised to 150°C. The reaction mixture was then kept at 150°C for about 1 hour longer.

WORKING UP OF THE REACTION MIXTURE

To convert excess phosphorus pentachloride, sulphur dioxide was passed in and $SOCl_2$ and $POCl_3$ formed were then distilled off. A subsequent distillation in vacuo at up to 137°C/13 mm Hg gave 660 g of a product mixture which according to the gas chromatogram contained 589 g (corresponding to 90.6% of theory) of trichloroethylidene-bis-(isocyanide-dichloride). The pure product was isolated by fractional vacuum distillation, whereupon trichloroethylidene-bis-(isocyanide-dichloride) distilled at 136–137°C/13 mm Hg. Recrystallisation from petroleum ether give colourless crystals of melting point 90°C. The empirical formula $C_4HCl_7N_2$ was confirmed by the mass spectrum.

The compound showed a characteristic IR spectrum with the following bands (in $cm^{-1}$); 2,910 w, 1,655 st, 1,625 st, 1,330 w, 1,310 m, 1,065 w, 1,050 m, 895 st, 810 st, 650 m, 595 m, 550 w, 535 w and 510 w (st = strong, m = medium, w = weak). The proton resonance spectrum in $CCl_4$ showed a signal at $\delta = 5.5$ ppm, relative to TMS.

EXAMPLE 2

750 g (3.6 mols) of phosphorus pentachloride in 1,200 ml of chloroform were reacted, in the manner described in Example 1, with 329.3 g (1.5 mols) of trichloroethylidene-bis-formamide. The reflux temperature during the addition of the trichloroethylidene-bis-formamide was 65°–67°C and was raised to about 150°C whilst distilling off chloroform. The reaction mixture was worked up as described in Example 1, giving, as the distillate, a product which contained 200 g (41% of theory) of trichloroethylidene-bis-(isocyanidedichloride).

EXAMPLE 3

1,000 g (4.8 mols) of phosphorus pentachloride in 1,000 ml of tetrachloroethylene were reacted with 439 g (2 mols) of trichloroethylidene-bis-formamide in the manner described in Example 1. The reflux temperature during the addition of the starting material was 118°C and was raised to about 150°C whilst distilling off tetrachloro - ethylene. After working up the reaction mixture as in Example 1, a distillate which contained 524 g (80.5% of theory) of trichloroethylidene-bis-(isocyanide-dichloride) was obtained.

EXAMPLE 4

500 g (2.4 mols) of phosphorus pentachloride in 800 ml of phosphorus oxychloride were reacted with 219.5 g (1 mol) of trichloroethylidene-bis-formamide in the manner described in Example 1. During the addition of the trichloroethylidene-bis-formamide the reflux temperature fell from an initial 112°C to 106°C. The reaction mixture was heated to 150°C whilst continuing to pass in chlorine, and whilst distilling off $POCl_3$. The working up of the reaction mixture was effected as in Example 1, giving, as the distillate, a product which contained 158 g (48.6% of theory) of trichloroethylidene-bis-(isocyanide-dichloride).

EXAMPLE 5

250 g (1.2 mols) of phosphorus pentachloride in 250 ml of carbon tetrachloride were first reacted with 110 g (0.5 mol) of trichloroethylidene-bis-formamide analogously to Example 1. After completion of the addition of the trichloroethylidene-bis-formamide, excess chlorine was additionally passed in for 1.5 hours until the reflux temperature reached 88°C. Thereafter, a vigorous stream of $SO_2$ was passed through the reaction mixture for about 0.5 hour at the reflux temperature. The distillation was carried out as in Example 1. 223 g of a distillate which, according to analysis by gas chromatography, contained 119 g (corresponding to 73% of theory) of trichloroethylidene-bis-(isocyanide-dichloride) were obtained.

EXAMPLE 6

439 g (2 mols) of trichloroethylidene-bis-formamide were added in small portions, over the course of about 1.5 hours, to a suspension, boiling under reflux, of 1,000 g (4.8 mols) of phosphorus pentachloride in 1,600 ml of carbon tetrachloride, whilst stirring and excluding moisture. Directly thereafter, excess chlorine was additionally passed in under reflux for about 1.5 hours. Excess $PCl_5$ was reacted by passing in $SO_2$ and the reaction mixture was then worked up by distillation, as in Example 1. The analysis by gas chromatography showed a yield of 360 g (55.4 % of theory) of trichloroethylidene-bis-(isocyanide-dichloride).

EXAMPLE 7

165 g (1.2 mols) of phosphorus trichloride were added dropwise over the course of about 1.5 hours to a suspension, saturated with chlorine gas and boiling under reflux, of 110 g (0.5 mol) of trichloroethylidene-bis-formamide in 250 ml of carbon tetrachloride, whilst excluding moisture and constantly continuing to pass in excess chlorine. The reaction mixture was worked up as described in Example 1. According to analysis by gas chromatography, the distillate contained 131 g (corresponding to 80.5% of theory) of trichloroethylidene-bis-(isocyanide-dichloride).

EXAMPLE 8

110 g (0.5 mol) of trichloroethylidene-bis-formamide were added in small portions, over the course of about 1 to 1.5 hours, to 500 ml of thionyl chloride, saturated with chlorine gas and boiling under reflux (about 70°C), whilst excluding moisture and constantly continuing to pass in excess chlorine (recognisable from the greenish colour of the issuing gas). The mixture was raised to about 150°C over the course of 3 to 4 hours, whilst constantly continuing to pass in excess chlorine and distilling off the thionyl chloride in the stream of chlorine, and was kept at this temperature for about an hour longer. The residual thionyl chloride was then stripped off in vacuo. The subsequent distillation of the residue was carried out as in Example 1. 66 g of a distillate, which according to analysis by gas chromatography contained 55 g (corresponding to 33.9% of theory) of trichloroethylidene-bis-(isocyanide-dichloride), were obtained.

EXAMPLE 9 a. Phytophthora test

To produce a preparation of active compound, 0.025 part by weight of trichloroethylidene-bis-(isocyanide-dichloride) was dissolved in a mixture of 4.7 parts by weight of acetone and 0.3 part by weight of alkylaryl polyglycol ether and the concentrate was diluted with 95 parts by weight of water.

Young tomato plants (Bonny best) with 2–6 foliage leaves were sprayed with this spray liquor until dripping wet. The plants remained in a greenhouse at 20°C and a relative atmospheric humidity of 70% for 24 hours. The tomato plants were then inoculated with an aqueous spore suspension of Phytophthora infestans. The plants were brought into a humidity chamber at 100% atmospheric humidity and a temperature of 18°–20°C.

After 5 days, the infection of the tomato plants was determined as a percentage of the untreated but likewise inoculated control plants. 0% means no infection and 100% means that the infection is exactly as great as in the case of the control plants.

At an active compound concentration of 0.025% the infection was only 27% compared to the infection of the untreated control plants.

b. Drosophila test

To produce a preparation of active compound, 1 part by weight of active compound was mixed with 3 parts by weight of acetone as the solvent and 1 part by weight of alkylaryl polyglycol ether as the emulsifier and the concentrate was diluted with water to the desired concentration.

1 $cm^3$ of the preparation of the active compound was applied with a pipette to a filter paper disc of 7 cm diameter. The disc was placed wet over the orifice of a glass vessel containing 50 vinegar flies (Drosophila melanogaster), and covered with a glass plate.

After one day, the destruction was determined in %, 100% means that all the flies were killed; 0% means that no flies were killed.

The active compound concentrations and results can be seen from the table which follows:

| Active compound concentration in % | Degree of destruction in % |
|---|---|
| 0.1 | 100 |
| 0.01 | 100 |
| 0.001 | 0 |

What is claimed is:
1. Trichloroethylidene-bis-(isocyanide-dichloride).